United States Patent [19]

Rentsch

[11] Patent Number: 5,251,639
[45] Date of Patent: Oct. 12, 1993

[54] CATHETER DEVICE

[75] Inventor: Hans Rentsch, Riverwoods, Ill.

[73] Assignee: Medline Industries, Inc., Mundelein, Ill.

[21] Appl. No.: 914,768

[22] Filed: Jul. 15, 1992

[51] Int. Cl.⁵ .............................................. A61B 5/00
[52] U.S. Cl. .................................... 128/761; 128/768
[58] Field of Search ............... 128/760, 761, 763, 767, 128/768; 604/189, 240, 243, 276, 279, 317, 326, 329, 331

[56] References Cited

U.S. PATENT DOCUMENTS

| | | | |
|---|---|---|---|
| 3,335,714 | 8/1967 | Giesy | 128/761 |
| 3,888,235 | 6/1975 | May et al. | 128/761 |
| 4,205,690 | 6/1980 | Layton | 128/768 |
| 4,256,132 | 3/1981 | Gunter | 604/189 |
| 5,112,327 | 5/1992 | Iinuma et al. | 604/240 |

Primary Examiner—Max Hindenburg
Attorney, Agent, or Firm—Laff, Whitesel, Conte & Saret

[57] ABSTRACT

A catheter device comprising a urine collection receptacle having a cap, a nozzle formed in the cap, a catheter tube adapted to extend through the aperture to deliver fluid to the urine collection receptacle, and means for releasably securing the catheter tube to the nozzle. The securing means allows the administering medical personnel to insert the catheter tube into the urine collection receptacle and remove the catheter tube from the receptacle without contacting directly the catheter tube. A label is pre-applied to the urine collection receptacle to permit marking for easy identification.

10 Claims, 1 Drawing Sheet

CATHETER DEVICE

FIELD OF THE INVENTION

The present invention relates to a catheterization device and, more particularly, to an improved catheterization device for obtaining a urine sample from a female or male.

BACKGROUND OF THE INVENTION

Catheters used to obtain uncontaminated urine samples from female or male patients are known in the art. One such catheter device, which is disclosed in U.S. Pat. No. 3,888,235 to May et al., comprises a urine collection receptacle with a removable cap to close the top end of the receptacle. The cap includes a nozzle that pivots from an upright, opened position to a horizontal, closed position. When the nozzle is in the opened position, a catheter tube may be inserted through the nozzle and into the collection receptacle to deliver fluid to the receptacle. After catheterization is complete, the catheter tube is removed from the urine collection receptacle, and the nozzle is pivoted downwardly to the closed position to seal the urine collection receptacle. The urine is then ready for laboratory processing.

The May et al. catheter has certain disadvantages because medical personnel must directly handle the catheter tube before, during and after catheterization. For example, prior to catheterization, the catheter tube must be inserted through the nozzle into the collection receptacle, and, to initiate catheterization, the catheter tube must be grasped in order to insert it into the patient. Such contact presents a contamination risk, especially if the gloves worn by the medical personnel are not sterile. Further, after catheterization, medical personnel must grasp the catheter tube in order to remove the catheter from the patient. Since urine often remains on the catheter tube after catheterization, there is a risk that urine may be transferred to the gloves of the medical personnel handling the catheter and thereby contaminate the medical personnel's body or clothing, or another medical apparatus situated nearby.

Another disadvantage of the May et al. device is that the catheter tube may not be tightly secured in the nozzle to prevent leaking or accidental dislodgment. Catheter tubes come in different sized diameters and if the diameter of the catheter tube does not fit tightly within the nozzle opening, the catheter tube may be dislodged from the nozzle. Moreover, even if the catheter tube is not dislodged, urine may leak from the collection receptacle if a tight fit is not provided between the catheter tube and nozzle opening.

An additional disadvantage of the May el al. device is that it does not provide a convenient method for marking the collection receptacle for easy identification.

Accordingly, it is an object of this invention to provide a catheterization device that can be used without the need for the administering physician or medical personnel to handle directly the catheter tube.

It is a further object of this invention to provide a catheterization device wherein the catheter tube can be securely attached to the urine collection receptacle.

It is a still further object of this invention to provide a catheterization device having a blank label pre-applied to the urine collection receptacle by silkscreen or paint.

SUMMARY OF THE INVENTION

In accordance with these and other objects, a catheter device is provided in the form of a urine collection receptacle, a catheter tube adapted to deliver fluid into the urine collection receptacle, and means, in the form of an adapter, for releasably and tightly securing the catheter tube to the urine collection receptacle. The catheter tube extends through the adapter, which fits over the nozzle on the urine collection receptacle.

By grasping the adapter and thus avoiding direct contact with the catheter tube, administering medical personnel can insert the catheter tube into the urine collection receptacle. Likewise, after the catheter tube has been secured to the collection receptacle, the catheter tube can be inserted into the patient without touching the catheter tube itself by grasping the adapter. After catheterization is complete, the catheter can be removed from the patient by grasping the adapter and pulling the adapter and catheter tube from the patient. The catheter tube can then be removed from the urine collection receptacle without touching the catheter tube itself.

The specific construction and dimensions of the adapter may vary depending on the type of urine collection receptacle employed. For example, an embodiment of an adapter that may be used with the catheter device of May et al. may comprise an upper cylindrical portion and a lower rectangular base. The cylindrical portion has a central bore to receive the catheter tube, and the base portion has a central cavity to receive the nozzle.

In addition, if desired, the outside of the receptacle may be treated to provide a blank label. This treatment may be applied by silkscreen, paint or the like and preferably is white. The administering medical personnel may write or otherwise mark identifying or other information on the label.

BRIEF DESCRIPTION OF THE DRAWINGS

The foregoing invention and its advantages may be readily appreciated from the following detailed description of the preferred embodiments, when read in conjunction with the accompanying drawings in which.

DETAILED DESCRIPTION OF THE PREFERRED EMBODIMENT

Figures 1, 2, 3, 4:
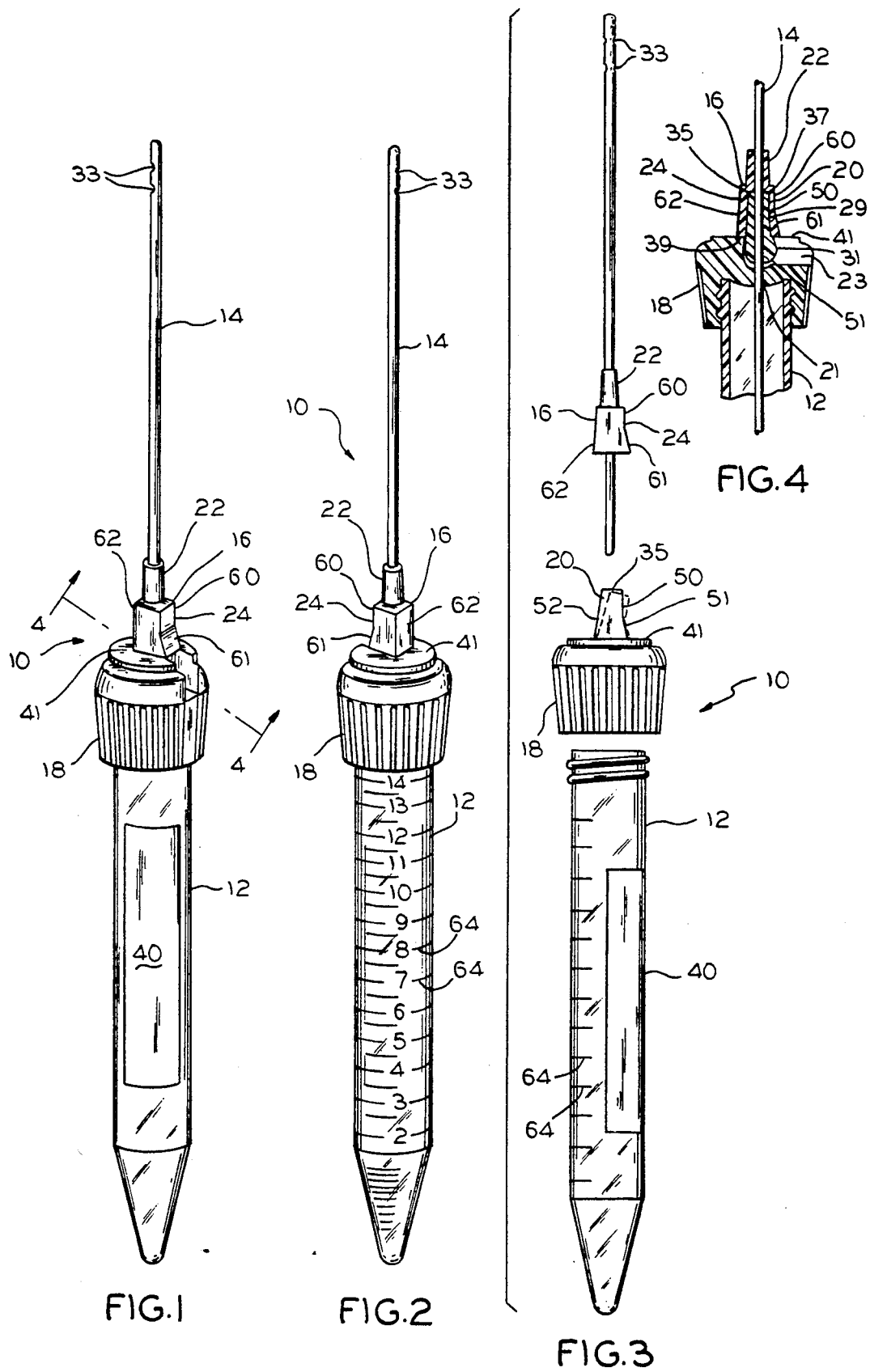
FIG. 1 is a front perspective view of a preferred embodiment of a catheter device in accordance with the present invention.
FIG. 2 is a rear perspective view of the catheter device of FIG. 1.
FIG. 3 is an exploded side view of the catheter device of FIGS. 1 and 2 showing the catheter tube and adapter removed from the urine collection receptacle and showing with dotted lines the pivoting action of the nozzle.
FIG. 4 is a partial cross section view take along lines 4-4 of FIG. 1.

FIGS. 1–4 show the catheter device 10 of the present invention comprising a urine collection receptacle 12, a catheter tube 14, and an adapter 16, which is constructed for mounting over the nozzle 20 of the urine collection receptacle 12. The receptacle 12 may be constructed similar to the device disclosed by May et al. U.S. Pat. No. 3,888,235, and may include a removable cap 18 for sealing the upper end of the receptacle 12. Nozzle 20 is pivotally mounted on the cap 18 for movement from an upright, opened position to a horizontal, closed position. Cap 18 is provided with aperture 21 which communicates with collection receptacle 12 when the cap is secured to the top of the collection receptacle. Catheter tube 14 is provided with a plurality of inlet openings 33 near the proximal end of catheter tube 14 to permit inflow of urine during catheterization.

Nozzle 20 is provided with an internal bore 29 which runs the entire length of the nozzle and opens at both ends of the nozzle to the exterior. When pivoted to the upright, opened position, internal bore 29 of nozzle 20 is aligned and communicates with aperture 21 located in cap 18 and a continuous passageway from the exterior of nozzle 20 to the interior of collection receptacle 12 is formed by bore 29 and aperture 21. When nozzle 20 is in the horizontal, closed position, nozzle 20 lies in slot 23 located in cap 18 and internal bore 29 is no longer aligned with aperture 21 so that bore 29 and aperture 21 are no longer in communication.

The nozzle in accordance with FIGS. 1-4 comprises a front wall 50, which has a flared portion 51 near its base, and a rear wall 52, which extends at a slight incline when the nozzle is in the open position, as best shown in FIG. 3. As shown in FIG. 4, a bulbous surface 31 of nozzle 20 seals the top of aperture 21 so that the interior of collection receptacle 12 is sealed from the exterior environment.

The configuration of adapter 16 should compliment the configuration of nozzle 20 so that the adapter can securely engage the nozzle, and, thus, may vary depending on the configuration and type of urine collection receptacle 12 employed. In the embodiment of FIG. 1-4, adapter 16 is a hollow, unitary structure comprising an upper cylindrical portion 22 and a base portion 24. The base portion 24 is adapted to be mounted on the nozzle 20 and compliments the configuration of nozzle 20. The base portion comprises a front wall 60, which has a flared portion 61, and a rear wall 62, which extends at a slight incline when the adapter is secured to nozzle 20 (see FIGS. 3 and 4). These walls correspond to the shape of the nozzle 20.

The interior of the hollow upper cylindrical portion 22 defines a continuous passageway so that the catheter tube 14 can be inserted into and extend through the adapter 16. When catheter tube 14 is inserted through the interior passageway of adapter 16, the tube is held in place by a tight frictional fit with the upper cylindrical portion 22 or by an adhesive applied to the tube or to the interior of the cylindrical portion 22. A tight frictional fit is more desirable, however, because it permits adjustment of the location of the adapter relative to the length of the tube after the tube has been inserted through the adapter. Adapter 16 may be constructed of any suitable material, such as, for example, a hard or soft plastic or rubber.

To secure catheter tube in collection receptacle 12, cap 18 is secured to the top of the receptacle and nozzle 20 is pivoted to its upright, opened position. The catheter tube and adapter assembly are then secured to collection receptacle 12 by applying base portion 24 of adapter 16 over the upright nozzle 20, which is received in a tight friction fit within the cavity formed by the hollow interior of the base portion 24. The upper end 35 of nozzle 20 firmly abuts against shoulder 37 formed in the interior of base portion 24 and the lower surface 39 of the base portion securely seats upon the top surface 41 of cap 18. A tight seal to prevent urine from leaking out of collection receptacle 12 when the catheter is in use is thus provided.

In preparation for catheterization, the administering medical personnel inserts the lower end of catheter tube 14 through adapter 16, and, then by grasping the adapter, inserts catheter tube 14 through the opened nozzle 20 and into urine collection receptacle 12, fitting the base portion 24 of the adapter 16 over the nozzle 20. During catheterization, adapter 16 securely holds catheter tube 14 in place relative to the urine collection receptacle 12 to prevent leaking from the collection receptacle 12 and dislodging of catheter tube 14. After completing catheterization, the administering medical personnel first removes the entire catheter assembly from the patient and then removes catheter tube 14 from urine collection receptacle 12 by grasping adapter 16 and pulling the adapter off the nozzle. Nozzle 20 is then pressed down to the closed position, and the urine sample contained in the urine collection receptacle 12 is ready for laboratory processing. Catheter tube 14 and adapter 16 may then be discarded. Accordingly, there is no need for the administering medical personnel to touch the catheter tube prior to, during or subsequent to catheterization.

A blank label 40 can be pre-applied to the urine collection receptacle 12 in any suitable manner, such as by silkscreen or paint. A physician or other medical personnel may write or mark identifying or other information on the label. In addition, if desired, graduations 64 may be provided along the length of urine collection receptacle 12, as shown in FIGS. 2 and 3.

The foregoing description is for purposes of illustration only and is not intended to limit the scope of protection accorded this invention. The scope of protection is to be measured by the following claims, which should be interpreted as broadly as the inventive contribution permits.

What is claimed is:

1. A catheter device comprising:
   a urine collection receptacle having an aperture;
   a catheter tube adapted to extend through the aperture to the receptacle to deliver fluid to the receptacle;
   means for sealing the aperture, the sealing means having an open and closed position whereby the sealing means in the open position provides access into the collection receptacle to receive urine and in the closed position closes the aperture;
   means for removably securing the catheter tube to the sealing means when the sealing means is in the open position, the securing means frictionally and releasably engaging both the catheter tube and the sealing means to hold the catheter tube and sealing means in secure relationship.

2. The catheter device of claim 1 wherein said securing means tightly surrounds both the catheter tube and sealing means.

3. The catheter device of claim 1 wherein said securing means comprises a first portion adapted to tightly surround the catheter tube and a second portion affixed to the first portion and adapted to tightly surround at least a portion of the sealing means, whereby the securing means retains the catheter tube in assembly with the sealing means.

4. The catheter device of claim 3 wherein the securing means has a longitudinal axis and the first portion is located at one end of the longitudinal axis and the second portion is located at the opposite end of the longitudinal axis, whereby the securing means aligns the catheter tube axially with the sealing means.

5. The catheter device of claim 3 wherein the sealing means includes a nozzle, the nozzle having an opened position to receive the catheter tube which provides access into the collection receptacle to receive urine and a closed position to preclude access into the collection receptacle, and the second portion of the securing means tightly surrounds the nozzle to retain the catheter tube in assembly with the nozzle.

6. The catheter device of claim 1 including a label permanently affixed to the collection receptacle for receiving identification or other types of markings and indicia.

7. The catheter device of claim 6 wherein said label is permanently affixed by means of silkscreening.

8. The catheter device of claim 6 wherein said label is permanently affixed by being painted on the collection receptacle.

9. The device of claim 1 wherein the first portion is cylindrical.

10. A catheter device of the type having a urine collection receptacle with an aperture to receive urine, means for sealing the aperture, said sealing means having an open position and a closed position whereby said sealing means in the open position provides access into the collection receptacle to receive urine and in the closed position closes the aperture, and a catheter tube adapted to extend through the aperture into the collection receptacle for delivering urine into the collection receptacle, wherein the improvement comprises means for removably securing the catheter tube to the sealing means when the sealing means is in the open position, the securing means removably engaging the catheter tube with the sealing means to hold the catheter tube and sealing means in secure relationship and wherein said securing means tightly surrounds the catheter tube and the sealing means.

* * * * *